(12) United States Patent
Agrawal et al.

(10) Patent No.: US 6,187,329 B1
(45) Date of Patent: **\*Feb. 13, 2001**

(54) VARIABLE PERMEABILITY BONE IMPLANTS, METHODS FOR THEIR PREPARATION AND USE

(75) Inventors: C. Mauli Agrawal; Kyriacos A. Athanasiou, both of San Antonio, TX (US)

(73) Assignee: Board of Regents of the University of Texas System, Austin, TX (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/996,708

(22) Filed: Dec. 23, 1997

(51) Int. Cl.[7] .................... A61F 2/02; A61F 2/28
(52) U.S. Cl. ............... 424/426; 424/424; 623/16
(58) Field of Search ................. 424/423, 424, 424/426; 623/16

(56) References Cited

U.S. PATENT DOCUMENTS

| | | | |
|---|---|---|---|
| 3,375,208 | 3/1968 | Duddy | 260/2.1 |
| 3,518,332 | 6/1970 | Sklarchuk . | |
| 3,536,796 | 10/1970 | Rock | 264/49 |
| 3,770,537 | 11/1973 | Elton | 156/77 |
| 3,923,936 | 12/1975 | Davis | 264/25 |
| 3,968,292 | 7/1976 | Pearman | 428/213 |
| 4,177,228 | 12/1979 | Prolss | 264/24 |
| 4,181,983 | 1/1980 | Kulkarni | 3/1 |
| 4,196,070 | 4/1980 | Chao et al. | 204/266 |
| 4,212,839 | 7/1980 | Funahashi | 264/45.3 |
| 4,294,753 | 10/1981 | Urist | 260/112 R |
| 4,386,129 | 5/1983 | Jacoby | 428/215 |
| 4,455,256 | 6/1984 | Urist | 260/112 R |
| 4,526,909 | 7/1985 | Urist | 523/115 |
| 4,563,489 | 1/1986 | Urist | 524/21 |

(List continued on next page.)

FOREIGN PATENT DOCUMENTS

| | | |
|---|---|---|
| XP-00211080 | 8/1978 | (JP) . |
| 55032651 | 3/1980 | (JP) . |
| XP-002110811 | 5/1989 | (RU) . |

OTHER PUBLICATIONS

Aspenberg, P., et al. "Bone morphogenetic protein induces bone in the squirrel monkey, but bone matrix does not" Thirty Ninth Annual Meeting, Orthopaedic Research Society 18, 101 (1993).

Ballock, T. T., et al. "Regulation of collagen expression in periosteal cells by three members of the TGF–B superfamily" Thirty Ninth Annual Meeting, Orthopaedic Research Society; 18,734 (1993).

(List continued on next page.)

Primary Examiner—Carlos A. Azpuru
(74) Attorney, Agent, or Firm—Robert W. Strozier

(57) ABSTRACT

The present invention involves filler for treating injured tissue sites made from compositions having variable permeability to bodily fluid to reduce the flow to these fluids (bleeding) from the site of injury into the surrounding tissue. The fillers are prepared by dispersing a pore-forming agent in a polymer with agitation. Density developing a variable concentration of pore-forming agent throughout the polymer through application of an external force acting on the mixture so that a portion of the filler has a variable impermeability to bodily fluids. After agitation and/or density development, the pore-forming agent is leached from the mixture to form a polymer matrix having variable permeability. Alternatively, the compositions can be made by fixedly combining a permeable material with an impermeable material to form a filler with reduced permeability to bodily fluid flow.

20 Claims, 5 Drawing Sheets

U.S. PATENT DOCUMENTS

| | | | |
|---|---|---|---|
| 4,596,574 | 6/1986 | Urist | 623/16 |
| 4,619,989 | 10/1986 | Urist | 530/417 |
| 4,634,720 | 1/1987 | Dorman et al. | 521/63 |
| 4,659,470 | 4/1987 | Caneba | 210/500.21 |
| 4,761,471 | 8/1988 | Urist | 530/350 |
| 4,789,732 | 12/1988 | Urist | 530/350 |
| 4,795,804 | 1/1989 | Urist | 530/350 |
| 4,857,456 | 8/1989 | Urist | 435/7 |
| 4,894,373 | 1/1990 | Young | 514/239.2 |
| 4,902,296 | 2/1990 | Bolander et al. | 623/16 |
| 4,902,511 | 2/1990 | Kronman | 424/423 |
| 4,904,478 | 2/1990 | Walsdorf et al. | 424/468 |
| 4,911,931 | 3/1990 | Baylink | 424/606 |
| 4,916,241 | 4/1990 | Hayward et al. | 549/313 |
| 4,921,697 | 5/1990 | Peterlik et al. | 424/85.5 |
| 4,939,131 | 7/1990 | Benedict et al. | 514/102 |
| 4,942,157 | 7/1990 | Gall et al. | 514/108 |
| 4,969,906 | 11/1990 | Kronman | 623/16 |
| 4,975,526 | 12/1990 | Kuberasampath, et al. | 530/350 |
| 5,102,917 | 4/1992 | Bedwell et al. | 521/61 |
| 5,162,114 | 11/1992 | Kuberasampath et al. | 424/423 |
| 5,171,574 | 12/1992 | Kuberasampath et al. | 424/423 |
| 5,286,763 | 2/1994 | Gerhart et al. | 514/772.4 |
| 5,324,519 | 6/1994 | Dunn et al. | 424/426 |
| 5,344,654 | 9/1994 | Rueger et al. | 424/423 |
| 5,366,756 | 11/1994 | Chesterfield et al. | 427/2.26 |
| 5,433,750 | 7/1995 | Gradinger | 623/16 |
| 5,460,621 | 10/1995 | Gertzman | 604/358 |
| 5,492,697 | 2/1996 | Boyan et al. | 424/422 |
| 5,516,532 | 5/1996 | Atala et al. | 424/548 |
| 5,522,895 | 6/1996 | Mikos | 623/16 |
| 5,607,474 | 3/1997 | Athanasiou et al. | 623/11 |
| 5,626,861 | 5/1997 | Laurencin et al. | 424/426 |
| 5,631,015 | 5/1997 | Bezwada et al. | 424/422 |
| 5,646,193 | 7/1997 | Brownscombe | 521/63 |
| 5,817,704 | 10/1998 | Shiveley | 521/63 |

OTHER PUBLICATIONS

Boehringer–Mannheim, Glowacki, J., et al. "The role of osteocalcin in osteoclast differentiation" J. Cellular Biochem. 45:292–302 (1991) Cytokines and Bone Metabolism, Gowen, ed. (CRC press, 1992).

Cook, S. D., et al. "Recombinant human osteogenic protein–1 (rhOP–1) heals segmental long–bone defects in non–human primates" Thirty Ninth Annual Meeting, Orthopaedic Research Society 18, 484 (1993).

Hunt, T. R., et al. "Healing of a segmental defect in the rat femur using a bone inducing agent (BIA) derived from a cultured human osteosarcoma cell line (SAOS–2)" Thirty Ninth Annual Meeting, Orthopaedic Research Society 18, 489 (1993).

Iwasaki, M., et al. "Bone morphogenetic protein–2 stimulates osteogenesis in high density culture of periosteum–derived cells" Thirty Ninth Annual Meeting, Orthopaedic Research Society 18, 483 (1993).

Miyamoto, S., et al. "Trans–filter bone induction in monkeys by bone morphogenetic protein" Thirty Ninth Annual Meeting, Orthopaedic Research Society 18, 99 (1993).

Ripamonti, U., et al. "Induction of bone in composites of osteogenin and porous hydroxyapatite in baboons" J.Plastic and Reconstructive Surg. 89:731–739 (1991).

VARIABLE PERMEABILITY BONE IMPLANTS, METHODS FOR THEIR PREPARATION AND USE

RELATED APPLICATIONS

This application is related to co-pending United States Patent Application Ser. No. 08/996,745 filed Dec. 23, 1997.

BACKGROUND OF THE INVENTION

1. Field of the Invention

This invention relates to implants having variable permeability for use in biological applications such as osteochondral autografts, tissue scaffolds, bone regeneration fillers or the like and methods for making the implants.

More particularly, this invention relates to compositions having variable or differential permeability where the compositions can have areas, regions and/or surfaces that are essentially or substantially impermeable, while other areas, regions or surfaces can be highly permeable, methods for making the compositions and to methods for using the compositions.

2. Background Information and Description of the Related Art

Successful design of an implant to replace skeletal tissue requires knowledge of the structure and mechanical properties of bone and an understanding of the means by which grafts become incorporated into the body. This information can then be used to define desirable characteristics of implants to ensure that the implants function in a manner comparable to organic tissue.

The mechanical properties of bone are related to the internal organization of the material. The porosity of cortical bone tissue (typically 10%) is primarily a function of the density of voids in the bone. In contrast, cancellous/trabecular bone is a network of small, interconnected plates and rods of individual trabeculae with relatively large spaces between the trabeculae. Trabecular bone has a porosity of 50–90% which is a function of the space between the trabeculae. The material properties of bone are based on determinations of the elastic modulus, compressive and tensile strengths.

As a general rule, bone is stronger in compression than in tension and cortical bone is stronger than trabecular bone. Ranges of reported elastic modulus have been from 10 MPa to 25 GPa (10 MPa to 2 GPa for cancellous bone; 4 to 25 GPa for cortical and cancellous bone); compressive strength between 40 and 280 MPa (40 to 280 MPa for cancellous bone; 138 to 193 MPa for cortical bone); and tensile strength between 3.5 MPa and 150 MPa (3.5 to 150 MPa for cancellous bone; 69 to 133 MPa for cortical bone).

Mechanisms by which bone may fail include brittle fracture from impact loading and fatigue from constant or cyclic stress. Stresses may act in tension, compression, and/or shear along one or more of the axes of the bone. A synthetic bone substitute should resist failure by any of these stresses at their physiological levels. A factor of safety on the strength of the implant may ensure that the implant will be structurally sound when subject to hyperphysiological stresses.

A graft may be necessary when bone fails and does not repair itself in the normal amount of time or when bone loss occurs through fracture or tumor. Bone grafts must serve a dual function: to provide mechanical stability and to be a source of osteogenesis. Since skeletal injuries are repaired by the regeneration of bone rather than by the formation of scar tissue, grafting is a viable means of promoting healing of osseous defects. Osteoinduction and osteoconduction are two mechanisms by which a graft may stimulate the growth of new bone. In the former case, inductive signals of little-understood nature lead to the phenotypic conversion of connective tissue cells to bone cells. In the latter, the implant provides a scaffold for bony ingrowth.

The bone remodeling cycle is a continuous event involving the resorption of pre-existing bone by osteoclasts and the formation of new bone by the work of osteoblasts. Normally, these two phases are synchronous and bone mass remains constant. However, the processes become uncoupled when bone defects heal and grafts are incorporated. Osteoclasts resorb the graft, a process which may take months. More porous grafts revascularize more quickly and graft resorption is more complete. After graft has been resorbed, bone formation begins. Bone mass and mechanical strength return to near normal.

Present methods for the repair of bony defects include grafts of organic and synthetic construction. Three types of organic grafts are commonly used: autografts, allografts, and xenografts. An autograft is tissue transplanted from one site to another in the patient. The benefits of using the patient's tissue are that the graft will not evoke a strong immune response and that the material is vascularized, which allows for speedy incorporation. However, using an autograft requires a second surgery, which increases the risk of infection and introduces additional weakness at the harvest site.

Further, bone available for grafting may be removed from a limited number of sites, for example, the fibula, ribs and iliac crest. An allograft is tissue taken from a different organism of the same species, and a xenograft from an organism of a different species. The latter types of tissue are readily available in larger quantities than autografts, but genetic differences between the donor and recipient may lead to rejection of the graft.

Synthetic implants may obviate many of the problems associated with organic grafts. Further, synthetics can be produced in a variety of stock shapes and sizes, enabling the surgeon to select implants as his needs dictate. Metals, calcium phosphate ceramics and polymers have all been used in grafting applications.

Biodegradable polymers are used in medicine as suture and pins for fracture fixation. These materials are well suited to implantation as they can serve as a temporary scaffold to be replaced by host tissue, degrade by hydrolysis to non-toxic products, and be excreted, as described by Kulkarni, et al., J. Biomedical Materials Research, 5, 169–81 (1971); Hollinger, J. O. and G. C. Battistone, "Biodegradable Bone Repair Materials," Clinical Orthopedics and Related Research, 207, 290–305 (1986), incorporated herein by reference.

Four polymers widely used in medical applications are poly(paradioxanone) (PDS), poly(dl-lactic acid) (PLA), poly(dl-glycolic acid) (PGA), and copolymers of dl-lactic acid and dl-glycolic acid (PLG). Copolymerization enables modulation of the degradation time of the material. By changing the ratios of crystalline to amorphous polymers during polymerization, properties of the resulting material can be altered to suit the needs of the application. For example, PLA is crystalline and a higher PLA content in a PLG copolymer results in a longer degradation time, a characteristic which may be desirable if a bone defect requires structural support for an extended period of time. Conversely, a short degradation time may be desirable if ingrowth of new tissue occurs quickly and new cells need space to proliferate within the implant.

Several patents have dealt with synthetic implants for use in reconstruction, repair and/or regeneration of tissues and/or organs and especially skeletal tissue including the following United States Patents.

U.S. Pat. No. 5,631,015 discloses a sustained release parenteral composition comprising an admixture of at least one drug to be delivered in a therapeutically effective amount and a bioabsorbable polymer containing one or more lactone monomers that is a liquid at body temperature, provided in an amount effective to sustain or extend the release rate of the drug and is incorporated herein by reference.

U.S. Pat. No. 5,626,861 discloses a method for making biodegradable composition involving mixing hydroxyapatite particles with a non-aqueous solution of a biodegradable, biocompatible polymer solvent; suspending particles of an inert waterleachable material in the solution, provided that the material is not soluble in the solution; removing the solvent; and removing the inert leachable material to yield a composite having pores and is incorporated herein by reference.

U.S. Pat. No. 5,516,532 discloses a demineralized ground bone or cartilage matrix where the phosphate content can be further reduced by treatment of the matrix with acid phosphatase, which removes residual organic phosphate and is incorporated herein by reference. The material is useful in a method of treatment of vesicouretal reflux and other disorders where a bulking agent is effective in correcting the defect.

U.S. Pat. No. 5,492,697 discloses a biodegradable implant for placement in nonunion bone fractures. The implant is a flat plate or disk having a thickness of between about 1 mm and about 15% of the length of the bone, interconnected micropores, and canals substantially equivalent in size and spacing to the naturally occurring Haversian canals and is incorporated herein by reference. The implant is formed form biodegradable polymers such as polylactic acid-polyglycolic acid copolymer by a gel casting technique followed by solvent extraction to precipitate the implant as a microporous solid.

U.S. Pat. No. 5,366,756 discloses a porous bioabsorable surgical implant material is prepared by coating particles of bioasborbable polymer with a tissue ingrowth promoter and is incorporated herein by reference.

U.S. Pat. No. 5,344,654 discloses a prosthetic device comprising a prosthesis coated with substantially pure osteogenic protein, which can be contained in a biocompatible polymer and is incorporated herein by reference.

U.S. Pat. No. 5,324,519 discloses a composition comprising a liquid formulation of a biodegradable, bioerodible, biocompatible thermoplastic polymer that is insoluble in aqueous or body fluid, and a biocompatible organic solvent that is miscible or dispersible in aqueous or body fluid and dissolves the thermoplastic polymer and is incorporated herein by reference.

U.S. Pat. No. 5,286,763 discloses bioerodible polymers which degrade completely into nontoxic residues over a clinically useful period of time, including polyanhydrides, polyorthoesters, polyglycolic acid, polylactic acid and copolymers thereof, are used for the delivery of bioactive agents directly into bone and is incorporated herein by reference.

U.S. Pat. Nos. 5,162,114, 5,171,574 and 4,975,526 discloses a matrix material comprising biocompatible mineral-free type I collagen, xenogenic to the host and biodegradable there within and is incorporated herein by reference.

Although these patents relate generally to various tissue scaffolds, biocompatible fillers or bone grafting compositions, there is still a need in the art for new filler compositions that provide increased functionality especially for the temporary or transient control of bleeding into tissue damaged areas while tissue reconstruction, regeneration and repair take place.

SUMMARY OF THE INVENTION

The present invention provides implants including substantially impermeable regions and permeable regions where the implants are designed to reduce bodily fluid flow such as bleeding from a site of injury into surrounding tissues, tissues regions, organs or organ regions. The implants are preferably composed of bio-compatible polymers and especially of bio-compatible and biodegradable polymers.

The present invention also provides methods for making implants having variable and/or differential permeability (and of course variable and/or differential porosity) including dispersing in a polymer matrix having a first density, at least one pore-forming agent having a second density and being insoluble in the polymer matrix. The dispersing of the agents in the matrix is preferentially carried out under controlled conditions where the controlled conditions include air-flow and optionally temperature, pressure, gas composition and/or humidity.

During or after the dispersing step, the agents are allowed to anisotropically distribute throughout the polymer matrix or portions thereof due to the action of an external force such as gravity. This anisotropic distribution results in formation of a portion of the composition which has reduced permeability than the remainder of the composition. Force development (anisotropic distributions of particles in the polymer matrix caused by the application of an external applied force) is preferably continued, generally with agitation, until a portion of the composition is substantially impermeable and/or non-porous. The resulting composition is then contacted with a leaching agent which leaches the particles from the polymer matrix leaving voids in matrix to form a composition with variable and/or differential permeability and/or porosity.

This invention also provides methods for coating, adhering or affixing to at least one portion of a surface of an implant composed of a composition having a first permeability and/or porosity, a material having a different permeability and/or porosity to form composite implants having simple or complex differential permeabilities and/or porosities. Again, it is preferred that the second composition be substantially impermeable to bodily fluids.

Using these two techniques, implants can be made that have complex arrays of permeabilities, either static or variable, within regions of or throughout the entire implant to bodily fluids in general or to constituents of bodily fluids. Thus, one part of the implant could allow permeation by small molecular constituents of bodily fluids, while other parts or regions could allow permeation by all constituents of bodily fluids. Of course, the implants can be designed so that disjoint (distinct) classes of constituents are allowed to migrate through different channels in the implant.

The implants of this invention can be used to prevent and/or treat diseases and disorders, such as diseases of the bone and connective tissue, infectious diseases, cancer, metabolic disorders and allergies. The implants of this invention can also be used for tissue regeneration useful in wound and organ repair, nerve regeneration, periodontium regeneration, and bone regeneration. The implants of this invention can also be used to alter physiological or biological activities of animals such as reproductive activity.

BRIEF DESCRIPTION OF THE DRAWINGS

The invention can be better understood with reference to the following detailed description together with the appended illustrative drawings in which like elements are numbered the same.

DESCRIPTION OF THE PREFERRED EMBODIMENTS

Figure 1:
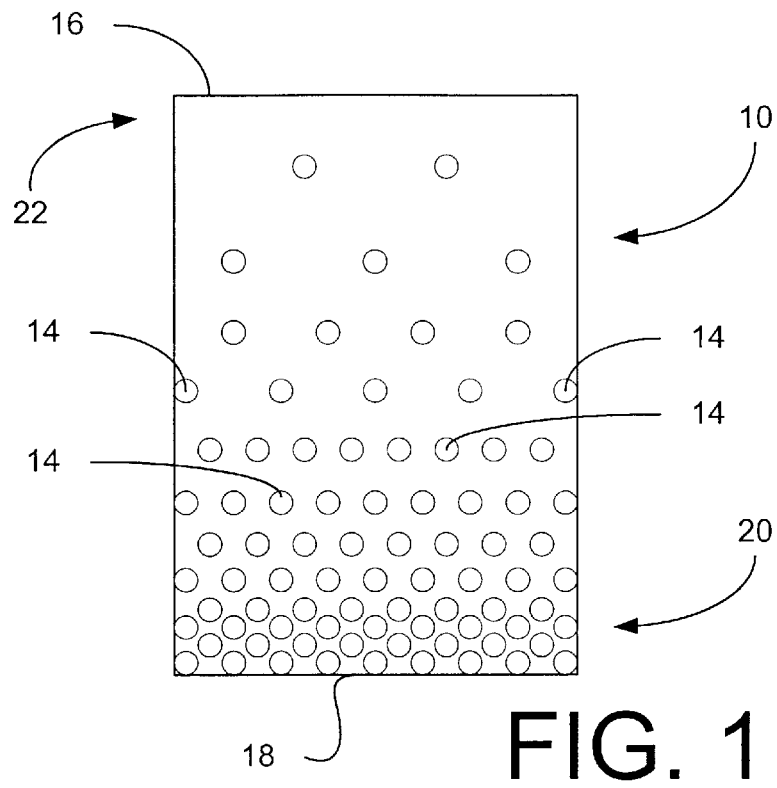
FIG. 1 is a cross-sectional view of a first embodiment of a bone filler plug prepared from a composition of the present invention having a single force induced variation in permeability and/or porosity.

The inventors have found that new implants can be prepared that have variable and/or differential permeability and/or porosity. The implants can have permeabilities to bodily fluids in general or to constituents thereof where the permeabilities vary across a desired profile of the implant or throughout the entire implant. Moreover, the implants can have porosities that also vary across a desired profile of the implant or throughout the entire implant. Implant permeability (or permeabilities to desired constituents of bodily fluids) can range from essentially or substantially impermeable to highly permeable to bodily fluids in general or to desired constituents of bodily fluids.

Preferably, the implants of the present invention have a surface or region of the implant that is substantially impermeable to bodily fluid so that blood flow from the injury into surrounding tissues is restricted or substantially prevented. Of course, when using bio-degradable polymer matrices, the impermeable surfaces or regions of the implant will become permeable to bodily fluids. But, by judicious selection of the polymer matrix, the impermeable surfaces or regions can be designed to remain substantially impermeable to blood flow for a sufficient time to allow blood flow to arrest via normal processes.

The implants can also be constructed to have different regions where each region has a different permeability or permeabilities that can vary across a profile of the region where the variation in permeabilities can range from essentially or substantially impermeable to highly permeable to the same or different class of constituents of bodily fluids. Of course, very complex composite structures can also be prepared having very complex permeability and/or porosity characteristics. Thus, implants of this invention can be prepared where different portions, parts, sub-structures, surfaces, regions or combinations thereof have different static or variable permeations to bodily fluids or constituents thereof so that the implant can direct different constituents into and out of different channels or diffusion pathways in the implant. For example, implants can be designed to channel cellular species preferentially, if not exclusively, to a first outlet via a first migration pathway in the implant and channel molecular species not only to the first outlet, but to other outlets through other migration pathways in the implant.

Moreover, the compositions of this invention can be formed not only with variable permeability and/or porosity as to a concentration of pores or void regions having one given size and/or shape, but also with variable permeability and/or porosity as to concentrations of pore sizes and/or pore shapes as well. Of course, these implants or at least the surfaces thereof should preferably be biocompatible with a target tissues site. In certain circumstances, it is also preferred that the polymeric components of the compositions be bioerodible or biodegradable as well.

The term implant includes all types of constructs for use in and/or on a living organism such as an human being. Implants, therefore, include, without limitation, tissue scaffolds, bone implants, cartilage implants, implantable drug or medication delivery systems, artificial skin, skin grafts, or other attachable or implantable constructs designed to facilitate tissue or organ regeneration, repair, reconstruction, and/or growth.

The implants or the compositions from which the implants derive can be made by dispersing one or more (at least one) leachable pore-forming agent in a polymer composition, generally a polymer melt or solution, to form a polymer matrix having the particles dispersed therein. Preferably, the agents have a density or densities different from the density of the polymer composition or the resulting polymer matrix. Preferably, the agents are particles that are substantially insoluble and non-decomposable in the starting polymer composition and in the final polymer matrix. However, the pore-forming agents can also be extractable/leachable polymers that can be either soluble or insoluble in the starting or final polymer matrix.

Because the polymer composition, into which the agents are dispersed, can be a solution or a melt, the density of the polymer matrix can change somewhat during preparation. Therefore, it is preferable that the density(ies) of the agents be different from the starting polymer composition and the final polymer matrix. The difference in density is what allows force developed anisotropic distributions of the agents in the polymer matrix during matrix preparation.

The step of dispersing is effectuated preferably by mechanical or sonic agitation or other similar agitation technologies. Of course, other mixing technologies can also be used in conjunction with mechanical or sonic agitation. The agitation is preferably carried out under controlled conditions where the conditions to be controlled include air-flow over the surface of the mold containing the composition and optionally temperature, pressure, gas composition and/or humidity. Of course, the agitation can be carried out in a closed atmosphere where control of air flow would not be as critical. Agitation is generally continued for a time sufficient for the solid particles to be distributed in the polymeric matrix to a desired degrees of dispersion.

Agitation, unlike conventional mixing, causes the particles to oscillate at a frequency corresponding to a frequency of the agitation. The oscillation will also have an amplitude and direction corresponding to an amplitude and direction of the agitation. This oscillation of the particles generally causing formation of a larger void volume than a volume of the particle itself, which is the minimum void volume that will be left behind after particle extraction. Depending on the frequency, direction and amplitude of agitation, the voids left behind after particle extraction can be substantially spherical or non-spherical (elongate, rod-like, tube-like, irregular shaped, ellipsoidal, or the like).

If the composition is subjected to an external force other than agitation, then a variation in the distribution of particles throughout the composition can be achieved. The external force can be static or variable and can be applied before, during, intermittently or after agitation. The difference in density is what allows force developed anisotropic distributions of the particles in the polymer matrix to be achieved. Of course, gravity is always acting on the composition during its preparation and particle gradient induced by gravity will result during any formation procedure. However, using the present method, the gradients in particle concentrations can be facilitated by either inducing a greater gravitational force or other applied forces such as centripetal force.

Moreover, the compositions can be subjected to a combination of forces so that variations in two dimensions or more dimensions can be induced in the compositions. Thus, the composition can be place in a cylindrical mold so that mold can be spun to achieve a radial anisotropic distribution of the particles at the same time at gravity is causing inducing an anisotropic distribution of particles in an axial direction.

Once the desired degree of dispersion is obtained, agitation can be stopped and the composition allowed to stand so that gravity and/or another applied force(s) can act on the composition to affect a segregation or variation in the concentration of the solid particles in the final polymeric matrix. For example, the mold containing the composition could be subjected to centripetal force by spinning the mold in a centrifuge or other similar device. Centripetal force will cause a radial anisotropic distribution of the particles dispersed in the matrix. The degree of anisotropy will depend on a magnitude of the centripetal force and on a period of time that the applied force acts on the composition. Other factors that control the degree and rate of segregation or anisotropic distribution of the particles are the viscosity of the polymer matrix, the temperature of the polymer matrix, the size and shape of the particles, or the like.

Of course, if a solvent(s) is used to make a polymer solution, then during agitation and subsequent segregation or force development, a certain amount of solvent will be removed from the polymer composition. However, to ensure move complete removal of solvent, the compositions is generally subjected to a reduced pressure environment with or without heating for a time sufficient to ensure substantial removal of solvent. Additionally, the temperature can be held constant, then ramped to a new temperature and held, etc. with or without the composition being subjected to a reduced pressure environment.

Once a desired degree of segregation or variation in the concentration of particles in the polymer matrix has been achieved and if necessary a desired degree of solvent removal has been achieved, then the composition is contacted with a leaching reagent that removes the particles from the polymer matrix leaving voids or pores therein to form a composition having variable permeability and/or porosity. The resulting composition will have a variation in the concentration of pores substantially identical to the variation in the concentration of the particles provided the leaching agent does not adversely affect the polymer matrix by causing voids to collapse or otherwise change shape.

After leaching, the polymer material is dried for a sufficient amount of time to remove any leaching medium that may be occupying the pores. Preferably, the polymer material is air-dried for approximately twenty-four hours followed by vacuum-drying for approximately forty-eight hours. Additionally, the composition can be subject to heating during the drying or solvent removal process.

Additionally, the compositions of the present invention can be subjected to post formation (after preparation and leaching) cross-linking reactions such as chemical or radiation curing. Preferably, the cross-linking forms biodegradable cross-links such as cross-linking with a biodegradable polyol or a polyacid.

The compositions of the present invention can be used to prepare implants and tissue carriers that are either biodegradable or bioerodible meaning that the composition substantially or completely dissolves over a period of time when exposed to aqueous environments including biological fluids found in animal or human bodies. During the time in which the implants or carriers dissolves, growing tissue can permeate the composition through pores in the composition thereby providing a scaffold into which rapid tissue regeneration can occur. The implants and/or carriers are particularly well suited for use in damaged or diseased tissue areas to promote repair or regeneration. Because the implants and/or carrier are preferably biodegradable, the carriers or implants provide interim support to the injured or damaged tissue site.

The bone implants of the present invention can be used in a method for repair and regeneration of bone injuries due to surgical procedures or traumatic injuries. The method includes inserting into a bone damaged site an implant having a substantially impermeable top surface or top region and a permeable lower region so that the impermeable top region is associated with an exterior of the bone and the lower region is associated with an interior of the bone. The placement of the implant or plug is to inhibit and preferably prevent bodily fluid flow from the interior of the bone to its exterior through the injury. Thus, the top surface should be substantially impermeable to bodily fluids such as blood, i.e., the implant should have a low hydraulic permeability. Generally, the implant should have a hydraulic permeability Preferably, the plug will fill the entire injury and the top surface of the implant will preferably conform to a contour of the bone surface into which the implant is inserted. Although the method has been described in connection with the treatment of bone injuries, the present implants can be equally well adapted to work as a filler, plug, implant or scaffolding for any tissue site where the implant's substantially impermeable surface, region, regions or surfaces are situated to inhibit or substantially prevent Polymers and Polymeric Compositions Suitable polymers for use in the present invention include, without limitation, biocompatible polymers that are preferably bioerodible by cellular action and/or are biodegradable by action of non-living body fluid components. Such polymeric substances include polyesters, polyamides, polypeptides and/or polysaccharides or the like.

Non-limiting examples of suitable biocompatible, biodegradable polymers, include polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly (amino acids), poly(methyl vinyl ether), poly(maleic anhydride), chitin, chitosan, and copolymers, terpolymers, or higher poly-monomer polymers thereof or combinations or mixtures thereof. The preferred biodegradable polymers are all degraded by hydrolysis.

Typically, the polymers will either be surface erodible polymers such as polyanhydrides or bulk erodible polymers such as polyorthoesters. Poly(1-lactic acid) (PlLA), poly(dl-lactic acid) (PLA), poly(glycolic acid) (PGA), polycaprolactones, copolymers, terpolymer, higher poly-monomer polymers thereof, or combinations or mixtures thereof are preferred biocompatible, biodegradable polymers. The preferred biodegradable copolymers are lactic acid and glycolic acid copolymers sometimes referred to as poly(dl-lactic-co-glycolic acid) (PLG). The co-monomer (lactide:glycolide) ratios of the poly(DL-lactic-co-glycolic acid) are preferably between about 100:0 to about 50:50 lactic acid to glycolic acid. Most preferably, the co-monomer ratios are between about 85:15 and about 50:50 lactic acid to glycolic acid. Blends of PLA with PLG, preferably about 85:15 to about 50:50 PLG to PLA, are also used to prepare polymer materials.

PLA, PlLA, PGA, PLG and combinations or mixtures or blends thereof are among the synthetic polymers approved for human clinical use. They are presently utilized as surgical suture materials and in controlled release devices, as well as in other medical and pharmaceutical applications. They are biocompatible and their degradation products are low molecular weight compounds, such as lactic acid and glycolic acid, which enter into normal metabolic pathways. Furthermore, copolymers of poly(lactic-co-glycolic acid) offer the advantage of a large spectrum of degradation rates from a few days to years by simply varying the copolymer ratio of lactic acid to glycolic acid.

To enhance bio-degradation of the polymers used in biological application, the compositions of the present invention can also include the addition of enzymes that can facilitate the biodegradation of the polymers used in the composition. Preferred enzymes or similar reagents are proteases or hydrolases with ester-hydrolyzing capabilities. Such enzymes include, without limitation, proteinase K, bromelaine, pronase E, cellulase, dextranase, elastase, plasmin streptokinase, trypsin, chymotrypsin, papain, chymopapain, collagenase, subtilisn, chlostridopeptidase A, ficin, carboxypeptidase A, pectinase, pectinesterase, an oxidoreductase, an oxidase or the like. The inclusion of an appropriate amount of such a degradation enhancing agent can be used to regulate implant duration.

Suitable Solvents

Suitable polymers can be combined with suitable organic solvents to form polymeric solutions. The solubility or miscibility of a polymer in a particular solvent will vary according to factors such as crystallinity, hydrophilicity, capacity for hydrogen-bonding and molecular weight of the polymer. Consequently, the molecular weight and the concentration of the polymer in the solvent are adjusted to achieve desired miscibility and/or viscosity. Preferred polymers are those which have a low degree of crystallinity a low degree of hydrogen-bonding, low solubility in water, and high solubility in organic solvents.

In general, the polymers are dissolved in a suitable organic solvent. Of course, the solvent should not adversely affect the polymer or the particulate solids and preferably should be a volatile organic solvent. The relative amount of solvent will have a minimal effect on the structure of the produced materials, but will affect the solvent evaporation time.

Solvents which may be used to make polymeric compositions of the invention include, without limitation, N-methyl-2-pyrrolidone, 2-pyrrolidone, C2 to C6 alkanols, propylene glycol, acetone, alkyl esters such as methyl acetate, ethyl acetate, ethyl lactate, alkyl ketones such as methyl ethyl ketone, dialkylamides such as dimethylformamide, dimethyl sulfoxide, dimethyl sulfone, tetrahydrofuran, cyclic alkyl amides such as caprolactam, decylmethylsulfoxide, oleic acid, propylene carbonate, aromatic amides such as N,N-diethyl-m-toluamide, and 1-dodecylazacycloheptan-2-one. Preferred solvents according to the invention include N-methyl-2-pyrrolidone, 2-pyrrolidone, dimethyl sulfoxide, acetone, and propylene carbonate. Preferred solvents are simple ketones such as acetone, chlorinated hydrocarbons such as methylene chloride, chloroform, methylethylketone, or the like.

Pore-Forming Agent

Suitable pore-forming agents include any substance, combination or mixture of substances that are insoluble or substantially insoluble in the polymeric composition or final polymer matrix (after solvent removal or after cooling) and can be removed from the polymer matrix leaving pores, voids or spaces in the matrix using any technique well-known in the art such as leaching with one or more leaching agents. Of course, the removal process should not significantly adversely affect the polymer matrix and should not significantly cause the polymer matrix to coalesce closing off or collapsing the volume occupied by the pore-forming agent or agents.

Suitable pore-forming agent for use in the present invention are preferably biocompatible, soluble in body fluids or capable of being biodegraded or bio assimilated in the body and relatively non-toxic. Non-limiting examples of suitable pore-forming agents, include: mono, di, tri and polysaccharides including erythrose, arabinose, xylose, ribose, lyxose, glucose, mannose, gulose, idose, talose, altrose, allose, sorbose, tagotose, fructose, sucrose, lactose, maltose, meliboise, cellobiose, trehalose, raffinose, melitose, or the like; amino acids; solid hydrocarbons and hydrocarbons containing one or more hetero atoms including naphthylene, benzoic acid, stearic acid or the like; carboxylic acids salts such as alkali metal salts including halide salts (fluorides, chlorides, bromides and iodides), carbonate salts, carboxylic acid salts, perchlorate salts or the like, alkaline metal salts such as including halide salts (fluorides, chlorides, bromides and iodides), carbonate salts, carboxylic acid salts, perchlorate salts or the like, ammonium salts including halide salts (fluorides, chlorides, bromides and iodides), carbonate salts, carboxylic acid salts, perchlorate salts or the like, phosphonium salts including halide salts (fluorides, chlorides, bromides and iodides), carbonate salts, carboxylic acid salts, perchlorate salts or the like, polymers such as hydroxylpropylcellulose, carboxymethylcellulose, polyethylene glycol, polyvinylpyrrolidone, or the like.

Besides the compounds noted above, suitable pore-forming agents include compounds that decompose up on heating, being subjected to strong electric or magnetic fields or compounds that can be selectively melted by sonic or microwave energy or that can be decomposed by exposure to radiation or other ionizing energy sources. The only requirement for the pore-forming agents in any of the applications to which the compositions of the present invention can be used is that the substances must be insoluble or substantially insoluble in the starting polymer composition or in the final polymeric matrix.

Again, the only requirement for any pore-forming agent is that the agent must not have appreciable solubility (preferably little to no solubility) in the polymer matrix or its precursor solution or melt and must be soluble (preferably very soluble) in a solvent in which the polymer matrix does not have appreciable solubility (preferably little to no solubility). However, the solvent can cause the polymer matrix to swell as long as the matrix does not substantially or significantly rearrange during the leaching process to either collapse forming pores or melt pores together.

The matrix is not considered to be significantly rearranged, if the pore-forming agent is removed with less than 35% loss in pore volume, i.e., no more than 35% of volume originally occupied by pore-forming agent(s) is lost during leaching assuming 100% leaching efficiency. The 35% target should be reduced appropriately for less than complete leaching efficiency. Thus, if leaching efficiency is only 85%, then the not significantly rearranged means that no more than 35% of the 85% pore volume is loss during leaching. The matrix is not considered to be substantially rearranged, if the pore-forming is removed with less than 15% loss in potential pore volume. Preferably, the rearrange or loss in potential pore volume due to leaching should be less than 10% and particularly less than 5%.

The concentration of pore-forming agent relative to polymer in the composition will vary according to the degree of pore-formation desired. Generally, this concentration will range from about 0.01 g to about 200 g of pore-forming agent per gram of polymer. Preferably, this concentration will range from about 10 g to about 150 g of pore-forming agent per gram of polymer. More particularly, this concentration will range from about 50 g to about 150 g of pore-forming agent per gram of polymer. Most particularly, this concentration will range from about 50 g to about 125 g of pore-forming agent per gram of polymer. And, most preferably, this concentration should be at least 50 g of pore-forming agent to polymer with the upper limit being the point at which not more agent can be incorporated into the polymer matrix.

Particle Leaching

The resulting polymeric matrix with the solid particles distributed variably therein is then leached to remove the dispersed solid particles. The leaching step is generally accomplished by immersing the matrix in a leach agent which is preferably a liquid in which the particles are soluble. Leaching is continued for a sufficient amount of time to allow leaching of substantially all of the particles, but which does not dissolve or detrimentally alter the polymer matrix.

For compositions composed of water insoluble or substantially water insoluble polymers or polymer mixtures, the preferred leaching agent is water, most preferably distilled-deionized water, which does not dissolve the polymer nor cause measurable hydrolysis of the polymer within the time required for processing. Preferably, the particle is leached out of the material in a vessel containing distilled-deionized water for a period of forty-eight hours for a polymer such as P1LA or ninety-six hours for PLG, and the water is changed approximately every twelve hours. The vessel can be placed in a heated water bath or incubator and shaken to enhance particle leaching. Most preferably, the vessel of water is placed in a water bath heated to approximately 37° C. and can be shaken at approximately 100 rpm to enhance the leaching process.

Permeability of the Polymer Matrix

Removal of the particles creates a polymer material having a plurality of pores, spaces or voids in the material formerly occupied and/or formed by the particles. Of course, these pores, spaces or voids can be either isotropically or anisotropically distributed throughout the matrix so that the matrix has substantially uniform, differential or variable permeation to components of complex fluid mixtures such as blood or other bodily fluids, complex reaction mixtures or complex mixtures in general. Moreover, these voids can be connected to form large interconnected cavities, channels, or other similar structures. Of course, the voids can also be isolated and disconnected. Thus, the compositions can be highly porous yet relatively impermeable to relatively non-porous and relatively permeable to highly porous and permeable.

In fact, the composition can have regions where the permeation or migration propensity of the composition to a given range of materials is very low to zero (i.e., less than about 20%, preferably less than about 10%, particularly less than about 5% and especially less than 1% with 0% being an ultimate goal) or very high (i.e., greater than about 50%, preferably greater than about 70%, particularly greater than about 80% and especially greater than 90%, with 100% permeation being an ultimate goal).

Such permeation can be measured either as to a particular component or using its hydraulic permeability given by the formula (Darchy's law) of equation (1):

$$K = \frac{h \Delta V}{A \Delta P \Delta t} \tag{1}$$

where K is the permeability, h is the height of the object being tested, $\Delta V$ is the volume change in the solution in contact with the object, A is the surface area of the object, $\Delta P$ is the pressure differential, and $\Delta t$ is the time. Darchy's law is designed to measure the permeation of a material to water, but the same principal can be used to define a permeability for other solvents or for constituents in a solution.

In the case of the plugs of the present invention, the permeable part(s) of the implant should have a hydraulic permeability K greater than or equal to about $1 \times 10^{-11}$, preferably greater than or equal to about $1 \times 10^{-9}$, particularly greater than or equal to about $1 \times 10^{-7}$ and especially greater than or equal to about $1 \times 10^{-5}$. Alternatively, the impermeable part(s) of the implants of the present invention should have a hydraulic permeability less than about $1 \times 10^{-13}$, preferably less than or equal to about $1 \times 10^{-15}$, particularly less than or equal to about $1 \times 10^{-17}$ and especially less than about $1 \times 10^{-19}$.

Moreover, to attain a permeability sufficient to allow macromolecular and cellular components of bodily fluids to permeate the implant, the implant or region thereof should have at least 20% of the pores in an interconnected state, preferably at least 30% of the pores in an interconnected state, particularly at least 40% of the pores in an interconnected state and especially at least 50% of the pores in an interconnected state. By interconnected state, the inventors mean that the pores are connected in such a way as to allow a give class of material to migrate from one pore into an interconnected cell. Generally, permeability increases when the number of interconnected pores increases.

Porosity of the Polymer Matrix

The size and/or quantity of a pore-forming agent incorporate in the polymer matrix, the distribution of the pore-forming agent within the polymer matrix, the frequency, direction and magnitude of agitation, among other factors, influence pore size and porosity of the polymer matrix. Where the implant is employed for the purpose of tissue regeneration, as for example, to promote guided tissue regeneration of periodontal tissue, it is preferred that the diameter of the pores in the matrix be effective to deter growth of epithelial cells into the polymer matrix of the implant, and enhance growth of connective tissue cells into the matrix.

Porosity is generally measured by the formula equation (2):

$$\text{Porosity} = \frac{V_v}{V_t} * 100 \qquad (2)$$

where $V_v$ is the void volume and $V_t$ is the total volume.

Preferably, the size of the pores and porosity of the matrix of the implant are distributed and interconnected to an extent sufficient to facilitate the diffusion of nutrients and other growth-promoting substances such as growth factors, to cells which have grown into the matrix. Of course, for those regions of the implants where diffusion is not desired, then the porosity should be relatively low or the pores should be disjoint. That is, the implant could have a high porosity and yet have low permeability to bodily fluid including water or the implant could have low porosity and in turn low permeability to bodily fluids.

Generally, the pores in the implants can range in diameter from about $1\mu$ to about $1000\mu$. However, larger and smaller pores can also be formed in the matrix using larger or smaller particulate materials. Preferably, the pores size ranges from about 50 to about 500 microns, more preferably between about 50 to about 400 microns, and most preferably between about 75 to about 300 microns. Of course, the implants of the present invention can have pores size distributions that are mono-modal, bi-modal or polymodal depending on the number of different pore-forming agents used and their particle size distributions and on agitation amplitude, direction and frequency.

It is further preferred that the degree of porosity of the matrix provides an implant which is capable of substantially maintaining structural integrity for a desired period of time without breakage or fracturing during use in those regions of the implant where permeation is preferred and remains substantially impermeable for a desired period of time to prevent swelling due to bleeding from an injured surface into and through the implant. The two period of time can be the same or different being judicious choices of pore-forming agents and polymers that have different densities so that a differential polymer composition can also be achieved during applied force material migration and segregation.

The size or diameter of the pores formed in the matrix may be modified by the size and/or distribution of the pore-forming agent within the polymer matrix. For example, pore-forming agents which are relatively insoluble in the polymer mixture, may be selectively included in the composition according to particle size to generate pores having a diameter which corresponds to the size of the pore-forming agent. Pore-forming agents which are soluble in the polymer mixture may vary the pore size and porosity of the polymer matrix according to the pattern of distribution and/or aggregation within the mixture and resulting polymer matrix. Again, the amplitude, direction and frequency of agitation will also affect the size and shape of the pores formed by the particles, especially rigid particles and particles insoluble in the polymer matrix.

It is further preferred that the matrix has a porosity between about 1 and about 99%, preferably between about 50 and about 99%, and particularly between about 75% and 99% in order to provide optimum cell and tissue ingrowth into the matrix and optimum structural integrity. Pore diameter and distribution within the polymer matrix may be measured, as for example, according to scanning electron microscopy methods by examination of cross-sections of the polymer matrix. Porosity of the polymer matrix may be measured according to any suitable method, as for example, mercury intrusion porosimetry, specific gravity or density comparisons, calculation from scanning electronic microscopy photographs, and the like. Additionally, porosity may be calculated according to the proportion or percent of water-soluble material included in the polymer composition. For example, a composition which contains about 30% polymer and about 70% water-soluble components will generate a polymer matrix having a porosity of about 70%.

Of course, because the present implants have variable permeability and/or porosity, the exact permeation and/or porosity of a given part or portion of the composition or object made therefrom can be tuned from substantially impermeable and/or non-porous to highly to completely permeable and/or porous to a given material or class of materials.

Incorporation of Other Materials Including Biologically-Active Agent

The implants of this invention may further contain other materials such as fillers to improve the strength of the polymer matrices, materials that will aid in degradation, anti-degradants such as anti-oxidants and anti-ozonants, biologically-active agent, colorants, chromophores or light activated (fluorescent or phosphorescent) tags or any other material that may alter or change the property of the compositions.

The addition of bioactive agents can provide the implants with biological, physiological or therapeutic effects in an animal and humans. Generally, such agents can be applied to the matrix after formation by dip or spray application. Additionally, the agents can be chemically or ionically bond to sites in the matrix. Preferably, these sites are biodegradable so that the agent can be release during biodegradation of the matrix.

Bioactive agents can be added, for example, to enhance cell growth and tissue regeneration, act for birth control, cause nerve stimulation or bone growth. The agent may also stimulate other desired biological or physiological activity within the animal. The biologically-active agent is preferably incorporated into the polymer matrix, and subsequently released into surrounding tissue fluids and to the pertinent body tissue or organ.

Biologically-active agents which may be used alone or in combination in the present compositions and implants include medicaments, drugs, or any suitable biologically-, physiologically- or pharmacologically-active substance which is capable of providing local or systemic biological or physiological activity in an animal, including a human, and which is capable of being released from the polymer matrix into an adjacent or surrounding aqueous fluid. The composite material can be used not only in the repair and replacement of bone but also in drug delivery, to bone or as a part of the repair process. Examples of materials which can be incorporated include antibiotics, chemotherapeutics and bone cell inducers and stimulators, including the general class of cytokines such as the TGF- beta superfamily of bone growth factors, the family of bone morphogenetic proteins, osteoinductors, and/or bone marrow or bone forming precursor cells, isolated using standard techniques.

If the biologically-active agent(s) are to be added to the polymer composition during preparation, then the agent(s) are preferably either insoluble or substantially insoluble in the leaching media. If the biologically-active agent(s) are to added to the polymer matrix after leaching of the pore-forming agent(s), then the biologically-active agent(s) can simply be applied to the matrix by standard dip or spray techniques followed by drying. Alternatively, the polymer matrix after removal of the pore-forming can also be treated with reagents that generate functional groups in the polymeric matrix to which biologically active agents can be chemically or physically attached. For chemically bound biologically active agents, the chemical bonding should be such that body enzyme systems or other active agents in bodily fluids can attach the bond and release the biologically active agent.

Suitable biologically-active agents also include substances useful in preventing infection at the implant site, as for example, antiviral, antibacterial, antiparasitic, antifungal substances and combinations thereof. The agent may further be a substance capable of acting as a stimulant, sedative, hypnotic, analgesic, anticonvulsant, and the like. The implants of this invention can contain large numbers of biologically-active agents either singly or in combination. Examples of these biologically-active agents include, but are not limited to: (1) anti-inflammatory agents such as hydrocortisone, prednisone, fludrotisone, triamcinolone, dexamethasone, betamethasone and the like; (2) antibacterial agents such as penicillins, cephalosporins, vancomycin, bacitracin, polymycins, tetracyclines, chloramphenicol, erythromycin, streptomycin, and the like; (3) antiparasitic agents such as quinacrine, chloroquine, quinine, and the like; (4) antifungal agents such as nystatin, gentamicin, miconazole, tolnaftate, undecyclic acid and its salts, and the like; (5) antiviral agents such as vidarabine, acyclovir, ribarivin, amantadine hydrochloride, iododeoxyuridine, dideoxyuridine, interferons and the like; (6) antineoplastic agents such as methotrexate, 5-fluorouracil, bleomycin, tumor necrosis factor, tumor specific antibodies conjugated to toxins, and the like; (7) analgesic agents such as salicylic acid, salicylate esters and salts, acetaminophen, ibuprofen, morphine, phenylbutazone, indomethacin, sulindac, tolmetin, zomepirac, and the like; (8) local anaesthetics such as cocaine, benzocaine, novocaine, lidocaine, and the like; (9) vaccines such as hepatitis, influenza, measles, mumps, rubella, hemophilus, diphtheria, tetanus, rabies, polio, and the like; (10) central nervous system agents such as tranquilizers, sedatives, antidepressants, hypnotics, B-adrenergic blocking agents, dopamine, and the like; (11) growth factors such as colony stimulating factor, epidermal growth factor, erythropoietin, fibroblast growth factor, neural growth factor, human growth hormone, platelet derived growth factor, insulin-like growth factor, and the like; (12) hormones such as progesterone, estrogen, testosterone, follicle stimulating hormone, chorionic gonadotrophin, insulin, endorphins, somatotropins and the like; (13) antihistamines such as diphenhydramine, chlorpheneramine, chlorcyclizine, promethazine, cimetidine, terfenadine, and the like; (14) cardiovascular agents such as verapamil hydrochloride, digitalis, streptokinase, nitroglycerine paparefine, disopyramide phosphate, isosorbide dinitrate, and the like; (15) anti-ulcer agents such as cimetidine hydrochloride, isopropamide iodide, propantheline bromide, and the like; (16) bronchodilators such as metaproternal sulfate, aminophylline, albuterol, and the like; (17) vasodilators such as theophylline, niacin, nicotinate esters, amylnitrate, minoxidil, diazoxide, nifedipine, and the like.

As the implants biodegrades and/or bioerodes, the biologically-active agent may be released from the matrix into the adjacent tissue fluids. Preferably, the biologically-active agent is released into the surrounding tissue fluids at a controlled rate. For example, the polymer matrix may be formulated to degrade after an effective and/or substantial amount of the biologically-active agent is released from the matrix. Release of a biologically-active agent having a low solubility in water, as for example a peptide or protein, may require the degradation of a substantial part of the polymer matrix to expose the agent directly to the surrounding tissue fluids. Thus, the release of the biologically-active agent from the matrix may be varied by, for example, the solubility of the biologically-active agent in water, the distribution of the biologically-active agent within the matrix, or the size, shape, porosity, solubility and biodegradability of the polymer matrix, among other factors.

The biologically-active agent may also be a substance, or metabolic precursor thereof, which is capable of promoting growth and survival of cells and tissues, or augmenting the activity of functioning cells, as for example, blood cells, neurons, muscle, bone marrow, bone cells and tissues, and the like. For example, the biologically-active agent may be a nerve growth promoting substance, as for example, a ganglioside, phosphatidylserine, a nerve growth factor, brain-derived neurotrophic factor, a fibroblast growth factor, and the like.

To promote tissue growth, the biologically-active agent may be either a hard or soft tissue promoting substance or combinations thereof. Suitable peptides and/or tissue growth promoting agents include, for example, fibronectin (FN), endothelial cell growth factor (ECGF), cementum attachment extracts (CAE), human growth hormone (HGH), a Periodontal ligament cell growth factor, fibroblast growth factor (FGF), animal growth hormones, platelet derived growth factor (PDGF), epidermal growth factor (EGF), protein growth factor interleukin-1 (IL-1), transforming growth factor (TGF beta-2), insulin-like growth factor II (ILGF-II), human alpha thrombin (HAT), osteoinductive factor (OIF), bone morphogenetic protein (BMP) or protein derived therefrom, demineralized bone matrix, and releasing factors thereof.

Further, the agent may be a bone growth promoting substance such as hydroxyapatite, tricalcium phosphate, a di- or polyphosphonic acid, an anti-estrogen, a sodium fluoride preparation, a substance having a phosphate to calcium ratio similar to natural bone, and the like. A bone growth promoting substance may be in the form, as for example, of bone chips, bone crystals or mineral fractions of bone and/or teeth, a synthetic hydroxyapatite, or other suitable form. The agent may further be capable of treating metabolic bone disorders such as abnormal calcium and phosphate metabolism by, for example, inhibiting bone resorption, promoting bone mineralization, or inhibiting calcification.

Non-limiting examples of bioactive agents can be found in the following issued U.S. patents: U.S. Pat. No. 4,939,131 to Benedict et al., U.S. Pat. No. 4,942,157 to Gall et al., U.S. Pat. No. 4,894,373 to Young, U.S. Pat. No. 4,904,478 to Walsdorf et al., and U.S. Pat. No. 4,911,931 to Baylink, U.S. Pat. No. 4,916,241 to Hayward et al., U.S. Pat. No. 4,921,697 to Peterlik et al., U.S. Pat. No. 4,902,296 to Bolander et al., U.S. Pat. No. 4,294,753 to Urist, U.S. Pat. No. 4,455,256 to Urist, U.S. Pat. No. 4,526,909 to Urist, U.S. Pat. No. 4,563,489 to Urist, U.S. Pat. No. 4,596,574 to Urist, U.S. Pat. No. 4,619,989 to Urist, U.S. Pat. No. 4,761,471 to Urist, U.S. Pat. No. 4,789,732 to Urist, U.S. Pat. No. 4,795,804 to Urist, and U.S. Pat. No. 4,857,456 to Urist, the disclosures of which are incorporated by reference herein.

Other non-limiting examples of biologically-active agents can be found in the following references, all of which are incorporated herein by reference: Cytokines and Bone Metabolism, Gowen, ed. (CRC press, 1992) material available from Boehringer-Mannheim, Glowacki, J., et al. "The role of osteocalcin in osteoclast differentiation" J. Cellular Biochem. 45:292–302 (1991); Ballock, T. T., et al. "Regulation of collagen expression in periosteal cells by three members of the TGF-B superfamily" Thirty Ninth Annual Meeting, Orthopaedic Research Society; 18,734 (1993); Ripamonti, U., et al. "Induction of bone in composites of osteogenin and porous hydroxyapatite in baboons" J. Plastic and Reconstructive Surg. 89:731–739 (1991); Ripamonti, U., et al. "Growth and morphogenetic factors in bone induction: role of osteogenin and related bone morphogenetic proteins" CRC Critical Reviews in Oral Biol. Med. 3:1–14 (1992); Ripamonti, U., et al. "Initiation of bone regeneration in baboons by osteogenin, a bone morphogenetic protein" Matrix; 12:40–55 (1992); Ripamonti, U., et al. "Xenogeneic osteogenin and demineralized bone matrices including human induced bone differentiation in athymic rats and baboons" Matrix 1 1:404–411 (1991); Cook, S. D., et al. "Restoration or large diaphyseal segmental defects in rabbits using recombinant human osteogenic protein (OP-1)" Combined meetings of Orthopaedic Research societies of USA, Japan and Canada 1, 66(1991); Miyamoto, S., et al. "Trans-filter bone induction in monkeys by bone morphogenetic protein" Thirty Ninth Annual Meeting, Orthopaedic Research Society 18, 99 (1993); Yasko, A. W., et al. "Comparison of recombinant human BMP-2 versus cancellous bone to heal segmental bone defects " Thirty Ninth Annual Meeting, Orthopaedic Research Society 18, 100 (1993); Aspenberg, P., et al. "Bone morphogenetic protein induces bone in the squirrel monkey, but bone matrix does not" Thirty Ninth Annual Meeting, Orthopaedic Research Society 18, 101 (1993); Iwasaki, M., et al. "Bone morphogenetic protein-2 stimulates osteogenesis in high density culture of periosteum-derived cells " Thirty Ninth Annual Meeting, Orthopaedic Research Society 18, 483 (1993); Cook, S. D., et al. "Recombinant human osteogenic protein-1 (rhOP-1) heals segmental long-bone defects in non-human primates" Thirty Ninth Annual Meeting, Orthopaedic Research Society 18, 484 (1993); and Hunt, T. R., et al. "Healing of a segmental defect in the rat femur using a bone inducing agent (BIA) derived from a cultured human osteosarcoma cell line (SAOS-2)" Thirty Ninth Annual Meeting, Orthopaedic Research Society 18, 489 (1993).

Implantation of the Objects from of the Polymer Matrix

In biological applications, the implants or implantable constructs of the present invention can be implanted into the body of an animal or human using any standard surgical technique. For the repair or replacement of bone, standard open surgery or minimally invasive surgical procedures such as arthoscopic surgical techniques can be used. The implants are generally implanted directly into the tissue site such as a bone site, where tissue repair or regeneration is desired, or the implants can be seeded with appropriate cells such as osteoblasts or osteoblast-like cells and then implanted. In the preferred embodiment, the implants will be pre-cast into a desired shape to conform to the requirements of the tissue site into which the implant will be inserted such as a site in a bone where treatment is needed.

Preferably, for bone implants, the implants are designed to have their substantially impermeable surface or region correspond to a portion of a bone surface being filled by the implant, while the portion of the implant within the bone structure itself is permeable to bodily fluids and cellular components so that bone regeneration can be facilitated. Thus, the implant will fill the bone defect and have a surface that conforms to the missing bone surface. The variable permeability of the implant reduces or prevents permeation of blood and other bodily fluids from the interior of the bone to the external tissues surrounding the bone injury site.

Referring now to FIG. 1, an object such as an implant or a membrane of an embodiment of the compositions of the present invention, generally, can be see to comprise a polymer matrix having dispersed therein pores. The pores can be seen to increase in frequency from a top of the object to a bottom of the object 10.

If the object is an implant, then the implant could be oriented in site of injuring or surgical removal either with the top in contact with the injuring site or with the bottom 18 in contact with the injuring site. If the orientation is the latter, then blood flow will be restricted from the injury site into surrounding tissue, yet the site of injury would be able to repair and regenerate using the enhanced permeability and/ or porosity of a lower region 20 of the object 10.

It should be recognized that the permeability and/or porosity of the object varying from its lower region 20 to its upper region 22. This variation is the result of an applied force acting on pore-forming agents during the preparation of the composition out of which the object 10 was formed. It should also be recognized that as a density or frequency of pores increases, the pores may not represent a single void as shown in FIG. 1, but adjacent pores may have points and/or areas of contact. When individual pores have points or areas of contact, then the volume of the resulting void area is the sum of the interconnected pores. Such interconnections can yield macro-voids and even regular or irregular channel-like structures in the matrix.

Preferably, as shown in FIG. 1, the top 16 of the bone filler plug 10 is pore free or impermeable. Of course, the upper region 22 could also simply be less porosity (fewer pores) than the lower region 20. Moreover, the composition can be such that the biodegradability (the rate at which biodegradation occurs) could also be different for the upper region 22 and the lower region 22. This result can be achieved by using two different polymers having different densities in the preparation of the composition so that gravity or whatever other applied force is used to induce a variation in particles density in the matrix can also induce a variation in the composition of the matrix due to differential sedimentation of the different polymers used to make the compositions.

Figure 2:
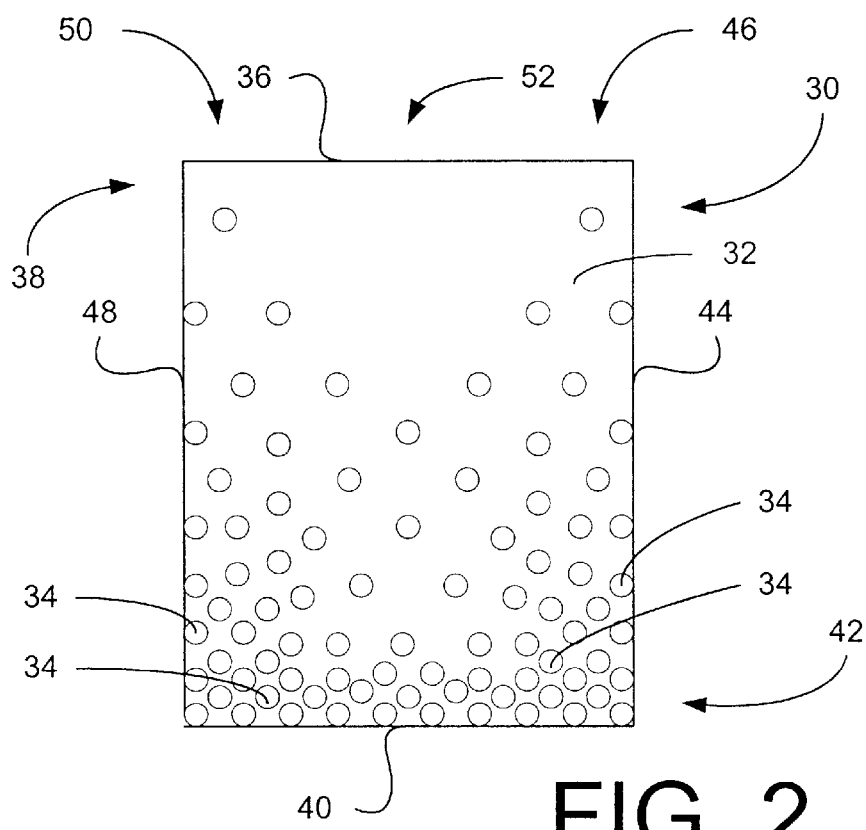
FIG. 2 is a cross-sectional view of a second embodiment of a bone filler plug prepared from a composition of the present invention having a double force induced variation in permeability and/or porosity.

Referring next to FIG. 2, another embodiment of a bone filler plug made from the compositions of the present invention, generally 30, can be see to comprise a polymer matrix 32 having dispersed therein pores 34. The bone filler plug 30 further includes a top 36, an upper region 38, a bottom 40, a lower region 42, a right side 44, a right region 46, a left side 48 and a left hand region 50. Unlike the bone filler plug 10 of FIG. 1, the bone filler plug 30 is the result of a preparation of a composition of the present invention in which two applied forces were used to induce a two dimensional variable distribution of pores in the matrix. Thus, the pores density not only variation from top to bottom, but also from left to right. It should be recognized that the composition from which the bone filler plug 30 was prepared used a static force like gravity and a radial force like centripetal force to induce the two dimensional variation in pore density. Again, the bone filler plug 30 has a substantially impervious or impermeable top or less permeable upper region and a less permeable (fewer pores) central region 52. Again, this composition can also be made with different polymers so that the resulting composition will not only have a two dimension variation in pore density, but also a two dimensional variation in composition.

Figure 3:
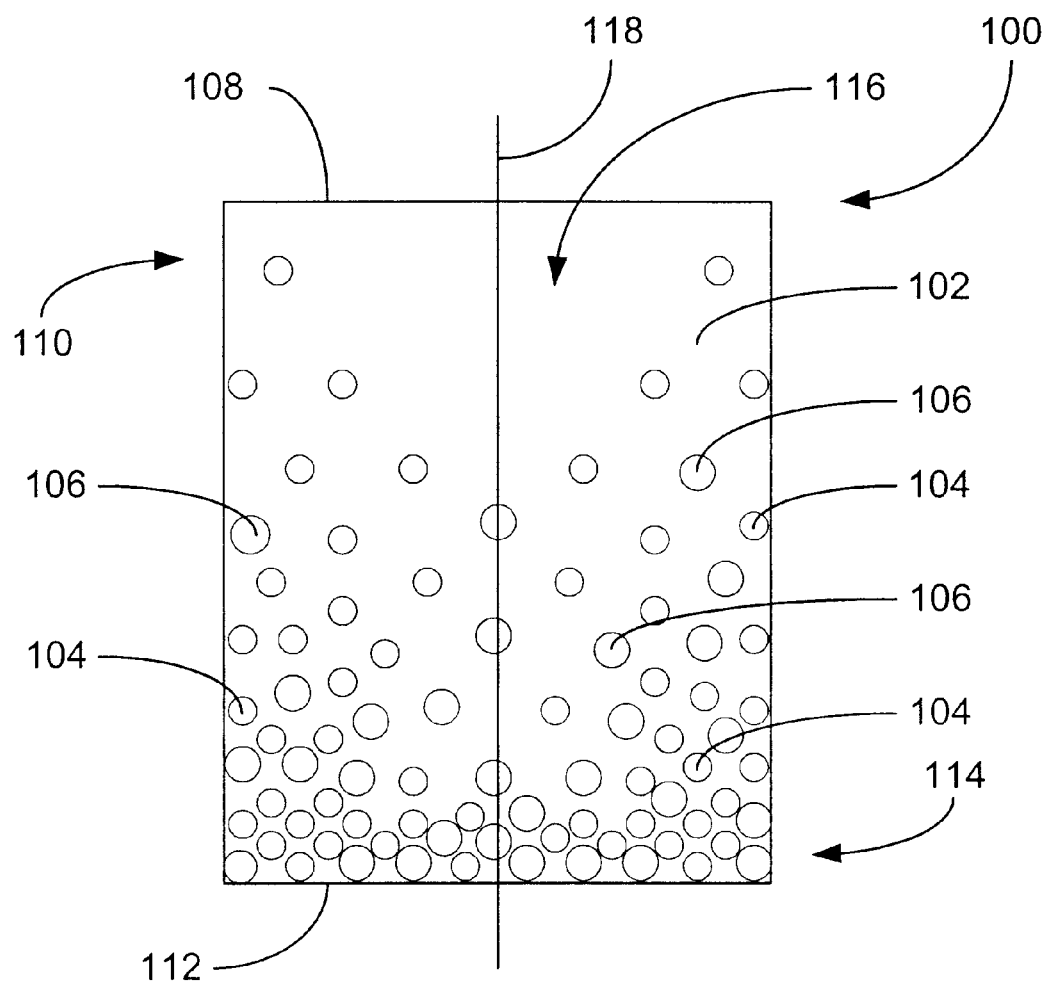
FIG. 3 is a cross-sectional view of another embodiment of a bone filler plug prepared from a composition of the present invention having a double force induced variation in permeability and/or porosity using two different sized pore-forming agents.

Referring now to FIG. 3, yet another embodiment of a bone filler plug made from a composition of the present invention, generally 100, can be see to comprise a polymer matrix 102 having dispersed therein a first type of pore 104 having a first size and a second type of pore 106 having a second pore size. The bone filler plug 100 further includes a top 108, an upper region 110, a bottom 112, a lower region 114 and a central region 116. The bone filler plug 100 derives from a composition in which two different sizes of a given pore forming agent was used. The composition has made using two forces acting along mutually perpendicular axis, i.e., gravity acting up and down coupled with spinning about a central axis 118 of the bone filler plug. Of course, the two forces do not have to act in a perpendicular arrangement for it is possible to spin the composition along any axis so that the angle between the centripetal and gravitional force vectors can be substantially zero degrees (parallel) or substantially 180° (perpendicular). Such an orientation can be easily accomplished by attached the machinery that spins and agitates the composition as it is being prepared and force developed on a platform that can be rotated through 180°.

It should be recognized that size and shape of the particles may affect the time it takes for force developed variations in the distribution of particles and/or different density polymers in the compositions. Thus, smooth and symmetric particles will generally move through the matrix at a faster rate under a developing force than will irregular, rough particles.

Moreover, larger particles will generally force develop faster than smaller particles provided the particles have similar smoothness and shape characteristics. The duration of application of the developing force will also depend on the viscosity of the matrix which in turn will depend on solvent, if any, concentration and temperature. Thus, raising the temperature of the composition will decrease development time.

Figure 4:
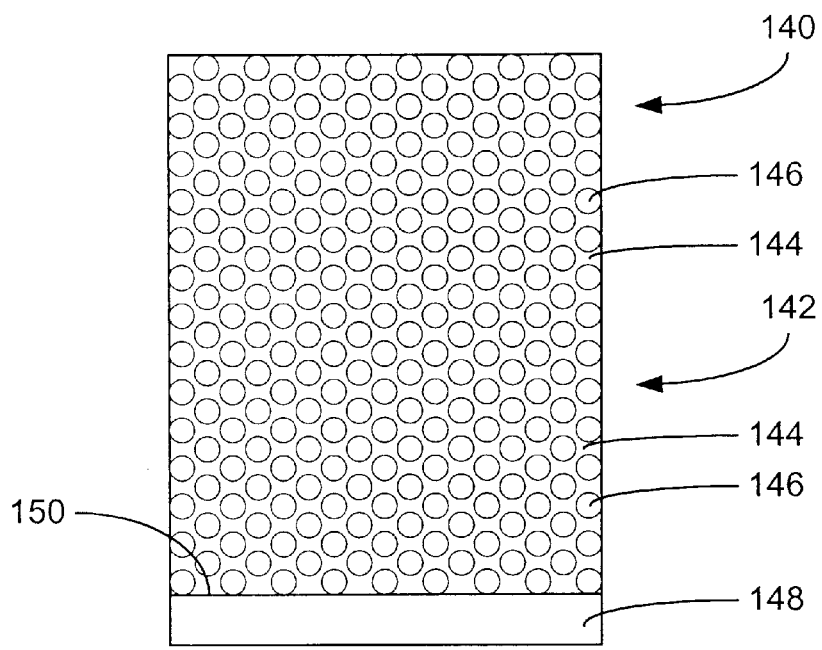
FIG. 4 is a cross-sectional view of a preferred embodiment of a composite bone filler plug of the present invention prepared from a highly porous and/or permeable composition having associated with one surface an impermeable or non-porous layer.
Figure 5:
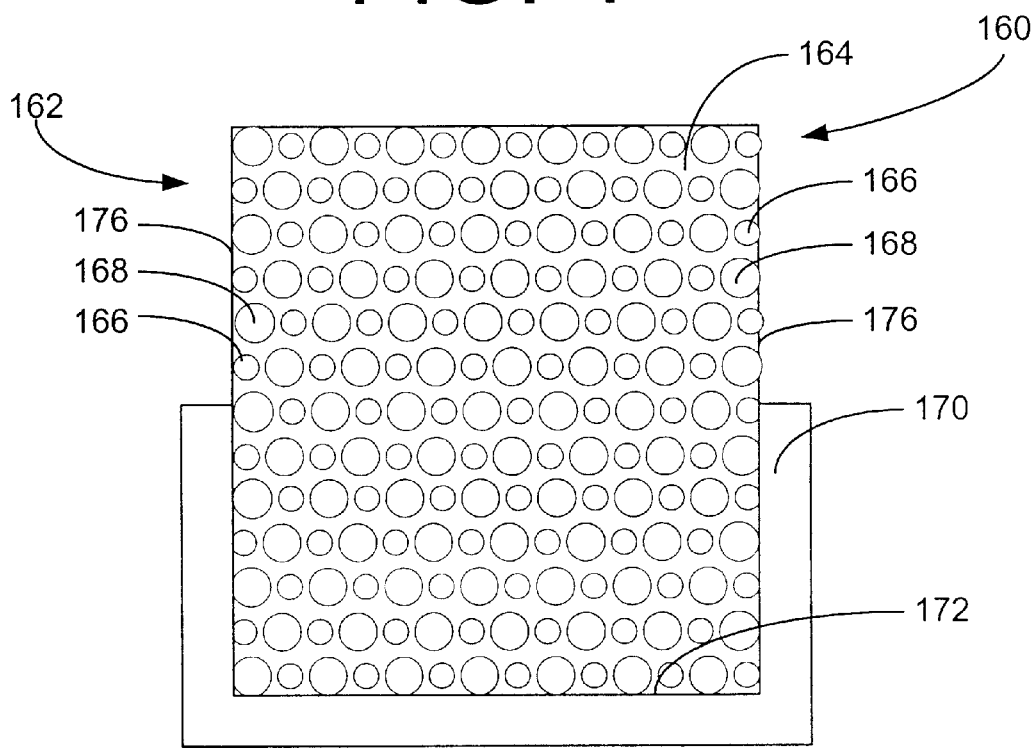
FIG. 5 is a cross-sectional view of another preferred embodiment of a composite bone filler plug of the present invention prepared from a highly porous and/or permeable composition having different pores sizes and having associated with certain surfaces thereof an impermeable or non-porous layer.

Looking next at FIGS. 4 and 5, two composite bone filler structures of the present invention generally 140 and 160. The composite 140 includes a top part 142 composed of a polymer matrix 144 having dispersed therein pores 146. Preferably, the pores 146 are dispersed uniformly throughout the matrix 144 as shown in the figure. It should be recognized that although the pores 146 are shown as circles of a given diameter, in actuality the pores will be of a given range of particle sizes and shapes depending on the nature of the particles used and the particles size distribution of the particles used.

The filler 140 further includes a bottom part or layer 148 composed of a different material which is either impervious or impermeable or has a different permeability than the permeability of the top part 142. This composite structure can be prepared by coating a uniformly permeable material or composition made any procedure known in the art or by coating a composition of the present invention with a material having a different permeability and/or porosity. Preferably, the bottom layer 148 is substantially impervious, non-porous or impermeable so that the final composited will be impermeable on one surface and permeable on other surfaces. Of course, the bottom layer 148 could extend over only a portion of a bottom 150 of the top part 142.

The composite 160 includes a top part 162 composed of a polymer matrix 164 having dispersed therein a first set of pores 166 and a second set of pores 168. Preferably, the pores 166 and 168 are dispersed uniformly throughout the matrix 164 as shown in the figure. It should be recognized that although the pores 166 and 168 are shown as circles of a given diameter, in actuality the pores will be of a given range of particle sizes and shapes depending on the nature of the particles used and the particles size distribution of the particles used.

The composite 160 further includes a part or layer 170 composed of a different material which is either impervious or impermeable or has a different permeability than the permeability of the top part 162. The layer 170 extends over a bottom 172 of the top part 162 and up onto a portion 174 of side surfaces 176 of the top part 162. Of course, if the composite 160 is cylindrical in shape, then the side surfaces 176 is actually only as single surface.

Again, this composite structure can be prepared by coating a uniformly permeable material or composition made any procedure known in the art or by coating a composition of the present invention with a material having a different permeability and/or porosity. Preferably, the layer 170 is substantially impervious, non-porous or impermeable so that the final composited will be impermeable on one surface and permeable on other surfaces.

Figure 6:
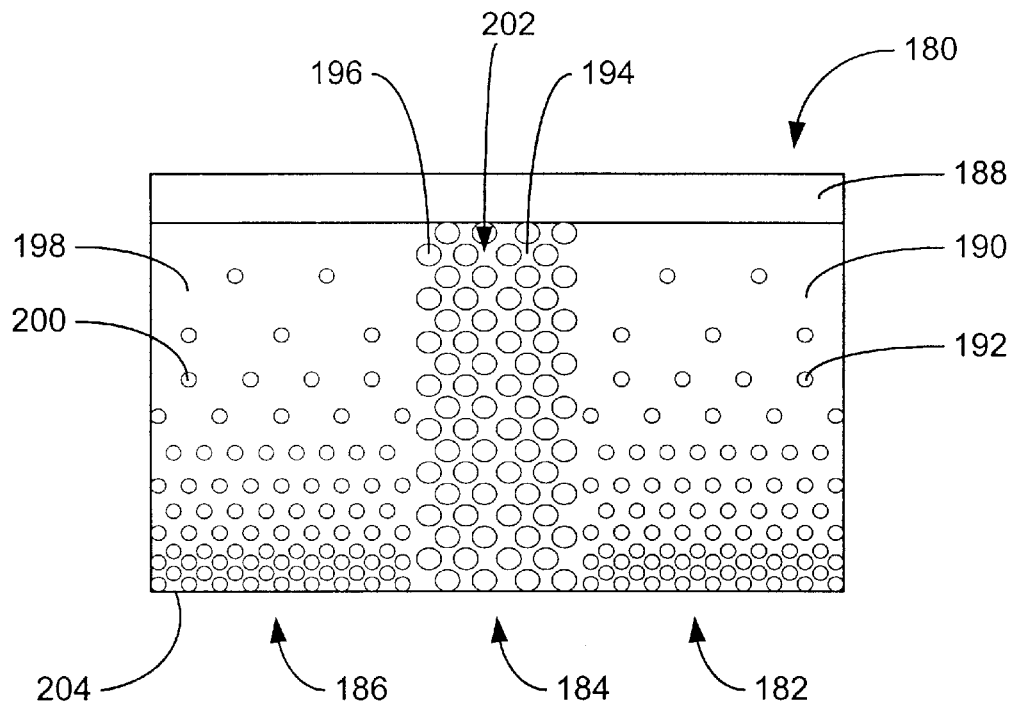
FIG. 6 is a cross-sectional view of another preferred embodiment of a composite bone filler plug of the present invention prepared from a highly porous and/or permeable composition sandwiched between two single force induced variable permeable and/or porous compositions of the present invention having associated with one surface thereof an impermeable or non-porous layer.
Figure 7:
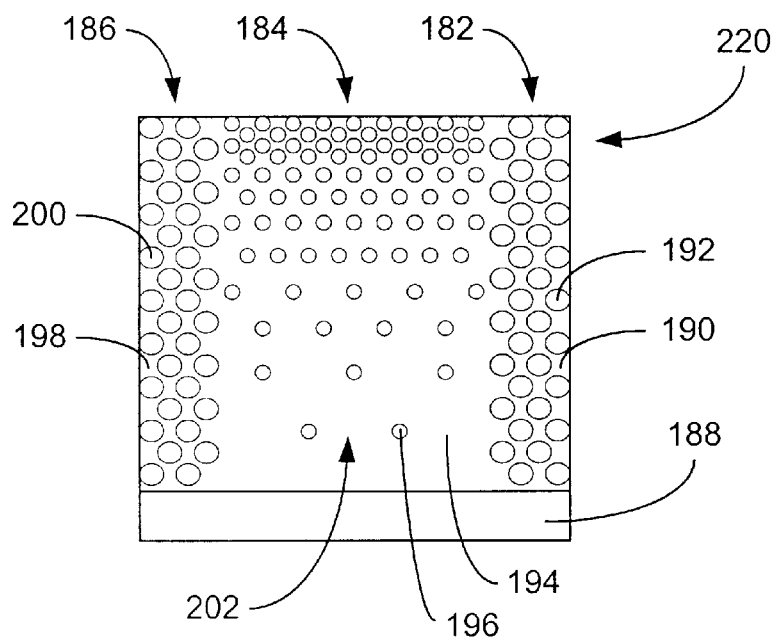
FIG. 7 is a cross-sectional view of another preferred embodiment of a composite bone filler plug of the present invention prepared from a single force induced variable permeable and/or porous compositions of the present invention sandwiched between two highly porous and/or permeable composition and having associated with one surface thereof an impermeable or non-porous layer.

Referring now to FIGS. 6 and 7, two more complex composites of the present invention are shown generally as 180 and 210. The composite 180 includes a first component 182, a second component 184, a third component 186 and an optional forth component 188. These components can be adhesively bonded together or integrally fused to each other where integrally fused means that an exchange of material across the interface has occurred or one material can simply be coated onto another material. Thus, the optional forth component 188 could simply represent a coating or layer over surfaces of other components. The component 182 includes a polymer matrix 190 having dispersed therein pores 192. The component 184 includes a polymer matrix 194 having dispersed therein pores 196. And, the component 186 includes a polymer matrix 198 having dispersed therein pores 200.

The components 182 and 186 are components having variable permeability and/or porosity that have been developed using a single applied force such as gravity. While component 184 has uniform porosity and/or permeability. Thus, by sandwiching component 184 between components 182 and 186, the composite 180 has an more porous interior region 202 do that the interior region 202 will allow the diffusion of larger species quickly into this area with diffusion into adjacent areas varying with the distance from a bottom 204 of the composite 180.

Alternatively, as shown in FIG. 7, the components 182 and 186 are now compositions that have a uniform permeability and/or porosity and the component 184 interposed therebetween having a variable permeability and/or porosity composition of the present invention. The composite 210 can also include a substantially impervious, nonporous and/or impermeable layer 188 deposited on a portion or an entire surface or as in FIG. 7, the layer 188 can be deposited over portion or one or more surface of the composite. Looking at FIGS. 4–7, it should be clear that many different composite fillers can be constructed to facilitate channeling of different biological species through different parts of the composite to either act to selectively direct certain biological agents to one tissue site and other to other tissue sites. Thus, composites could be designed to direct growth factors to all tissues in contact with permeable areas of a composite, while directing antibiotics to one tissue site and not other tissue sites.

The composition could first be gravity developed, then centripetally developed along one axis and then along another axis. Moreover, if some of the pore forming agents are electrically active (charged ion pairs), then electrical developing can be performed on the electrically active agents after gravity and/or centripetal developing have been performed. This same procedure could be used for magnetically active agents (agent that will move when subjected to an external magnetic field). Again, it must be emphasized that electrically and magnetically mobile pore-forming agents must be capable of being leached from the matrix after development. In the case of ion pairs, generally water leaching will remove these species. In the case of magnetically active agents, if the agents can be leached by acid, base or chelating solutions that do not significantly decompose the polymer matrix, then the agents can be used in the present invention to make composition having variable permeability and/or porosity.

Figure 8:
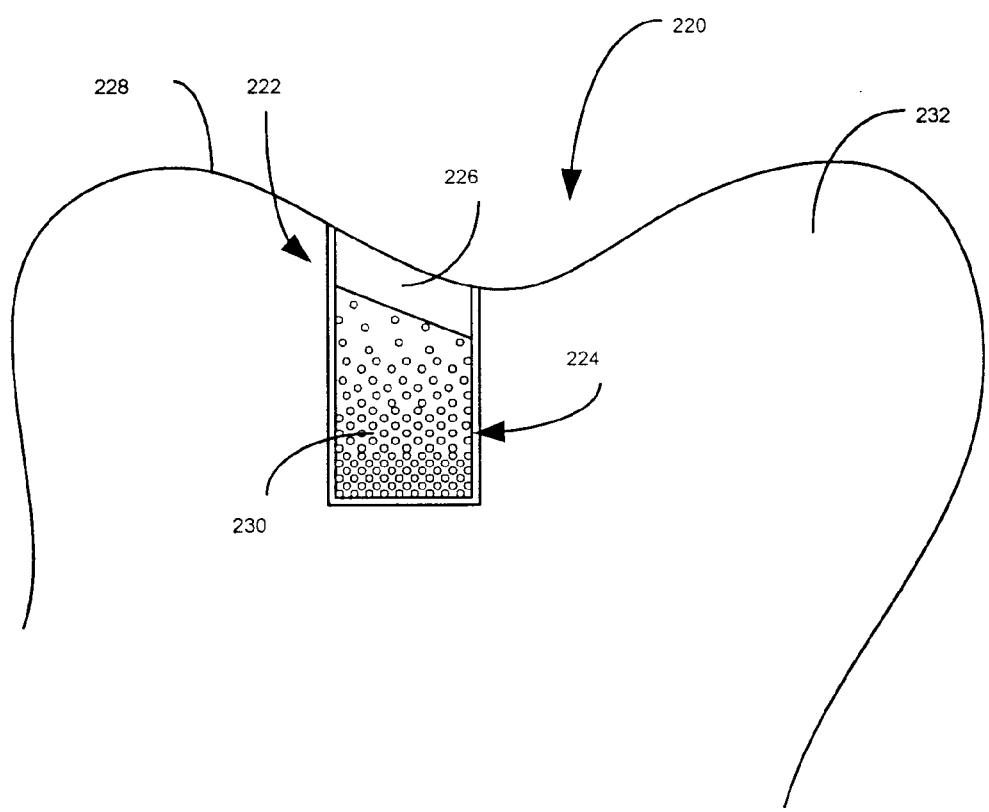
FIG. 8 is a cross-sectional view of a bone plug of the present invention inserted into a injured bone site.

Referring now to FIG. 8, a section of bone 220 is shown with a injury site 222 and a filler 224 of the present invention inserted therein. The filler 224 is inserted into the injury site 222 so that its impermeable portion 226 is associated with a surface contour 228 of the bone 220, while its permeable portion 230 is associated with an interior 232 of the bone 220. A surface 234 of the impermeable portion 226 is designed to conform to the surface contour 228 of the bone. This manner of inserting the filler 224 into the bone 220 reduces blood flow from the interior 232 of the bone 220 through the filler 224 into to surroundings 236.

EXAMPLES

The following examples are include for the sake of completeness of disclosure and to illustrate the methods of making the compositions and composites of the present invention as well as to present certain characteristics of the compositions, but in no way are these examples included for the sake of limiting the scope or teaching of this disclosure.

Example 1

This example illustrates the preparation of a 7 mm by 7 mm bone filler plug using a 50:50 copolymer of lactic and glycolic acid.

0.125 grams of a 50:50 a lactic acid/glycolic acid copolymer was dissolved in 3 mL of acetone. The solution was added onto an appropriate amount of sodium chloride particles in a Teflon mold. The mixture was then agitated on a Vortex shaker for 5 minutes under controlled airflow conditions. Shaking was stopped. The composition was then placed under house vacuum for 24 hours. The composition was then placed under heat and vacuum of an additional 24 hours. During the heat and vacuum treatment, the majority to substantially all of the solvent is removed and the particles are allowed to settle due to the action of gravity on the composition. Using an appropriate sized cutter, a cylindrical construct having a diameter of 7 mm and a height of 7 mm was cut from the composition. The construct or plug was placed in ultra pure water for 72 hours to remove the sodium chloride particles, exchanging the water every 24 hours.

Example 2

This example illustrates the preparation of a 7 mm by 7 mm uniform porosity bone filler plug using a 50:50 copolymer of lactic and glycolic acid having a non-porous coating applied thereto.

0.125 grams of a 50:50 a lactic acid/glycolic acid copolymer was dissolved in 3 mL of acetone. The solution was added onto an appropriate amount of sodium chloride particles in a Teflon mold. The mixture was then agitated on a Vortex shaker for 5 minutes under controlled airflow conditions. A second portion of sodium chloride was added to the surface of the composition and shaking was continued. The composition was then placed under house vacuum for 24 hours with shaking. The composition was then placed under heat and vacuum of an additional 24 hours with shaking. Using an appropriate sized cutter, a cylindrical construct having a diameter of 7 mm and a height of 7 mm was cut from the composition. The construct or plug was placed in ultra pure water for 72 hours to remove the sodium chloride particles, exchanging the water every 24 hours. The construct was then coated with a non-porous coated of the copolymer by dipping one end of the plug in a 10% by weight solution of the copolymer. The coated plug was then vacuum treated for 24 hours to remove the solvent in the coating.

Example 3

This example illustrates the preparation of plugs having a uniform porosity and/or permeability which are then coated by a non-porous, impermeable coating.

2.3 grams of 50/50 poly(DL-lactide-co-glycolide) (Birmingham Polymers, Birmingham) with inherent viscosity of 0.69 dl/gm was dissolved in 12.3 mL of pure acetone. The solution was stirred with a 25 mm stir bar in a 28 mm diameter Teflon (DuPont Chemical Company, Wilmington, Del.) beaker until complete dissolution using a Thermix Stirring Hot Plate Model 310T (Fischer Scientific, Pittsburgh, Pa.). In a 40 mm×40 mm×23 mm Teflon well, 9.25 grams of a particular NaCl having particles size between about 0.25 mm to about 0.50 mm was evenly spread. The polymer solution was poured evenly onto the salt in the well.

The mold was then placed in an air-flow chamber, where it was agitated by a Thermolyne Maxi Mix II (Barnstead/Thermolyne, Dubuque, Iowa) working at maximum power for 6 minutes. The air flow chamber is an enclosed box with variable control fans and filters so that the rate of air passing through the chamber can be controlled. Another 9.25 grams of NaCl was added to the well. The mold was then agitated for an additional 4 minutes. Two grams of salt was then evenly poured over the implant in the well. Agitation was continued for an additional 3 minutes. The mold was left in the air-flow chamber for 24 hours. It was then placed in a heated vacuum at 45° C. and 5000 mTorr for 24 hours. After the 24 hour period, the implants were punched out of the mold with a 10 mm diameter punch. The implants were then placed in distilled water for 72 hours. The water was replaced once daily. The implants were placed in a desiccator at room temperature after they were removed from the water.

Once highly permeable scaffolds were made, one side of 3 constructs were dipped in a 2 mm thick PLG/acetone solution for 5 s. The constructs were then dried in the air-flow chamber for 24 hours.

Example 4

This example illustrates the preparation of plugs having a uniform porosity and/or permeability which are then spray coated with a non-porous, impermeable coating.

One side of 3 uniformly permeable constructs of Example 3 were rendered essentially impermeable by spraying an PLG/acetone solution using an atomizer spray gun onto the desired side of the constructs.

Example 5

This example illustrates the preparation of plugs having a uniform porosity and/or permeability through the bulk of the composition and a substantially non-porous, impermeable thin top layer.

2.3 grams of 50/50 poly(DL-lactide-co-glycolide) (Birmingham Polymers, Birmingham) with inherent viscosity of 0.69 dl/gm was dissolved in 12.3 mL of pure acetone. The solution was stirred with a 25 mm stir bar in a 28 mm diameter Teflon (DuPont Chemical Company, Wilmington, Del.) beaker until complete dissolution using a Thermix Stirring Hot Plate Model 310T (Fischer Scientific, Pittsburgh, Pa.). In a 40 mm×40 mm×23 mm Teflon well, 9.25 grams of a particular NaCl having particles size between about 0.25 mm to about 0.50 mm was evenly spread. The polymer solution was poured evenly onto the salt in the well.

The mold was then placed in an air-flow chamber, where it was agitated by a Thermolyne Maxi Mix II (Barnstead/Thermolyne, Dubuque, Iowa.) working at maximum power for 6 minutes. The air flow chamber is an enclosed box with variable control fans and filters so that the rate of air passing through the chamber can be controlled. Another 9.25 grams of NaCl was added to the well. The mold was then agitated for an additional 4 minutes. The mold was left in the air-flow chamber for 24 hours. It was then placed in a heated vacuum at 45° C. and 5000 mTorr for 24 hours. After the 24 hour period, the implants were punched out of the mold with a 10 mm diameter punch. The implants were then placed in distilled water for 72 hours. The water was replaced once daily. The implants were placed in a desiccator at room temperature after they were removed from the water. Nine constructs were produced having one relatively impermeable side (the top side).

Example 6

This example illustrates the preparation of plugs having a uniform porosity and/or permeability through the bulk of the composition and a substantially non-porous, impermeable thin top layer.

2.3 grams of 50/50 poly(DL-lactide-co-glycolide) (Birmingham Polymers, Birmingham) with inherent viscosity of 0.69 dl/gm was dissolved in 12.3 mL of pure acetone. The solution was stirred with a 25 mm stir bar in a 28 mm diameter Teflon (DuPont Chemical Company, Wilmington, Del.) beaker until complete dissolution using a Thermix Stirring Hot Plate Model 310T (Fischer Scientific, Pittsburgh, Pa.). In a 40 mm×40 mm×23 mm Teflon well, 9.25 grams of a particular NaCl having particles size between about 0.25 mm to about 0.50 mm was evenly spread. The polymer solution was poured evenly onto the salt in the well.

The mold was then placed in an air-flow chamber, where it was agitated by a Thermolyne Maxi Mix II (Barnstead/Thermolyne, Dubuque, Iowa working at maximum power for 6 minutes. The air flow chamber is an enclosed box with variable control fans and filters so that the rate of air passing through the chamber can be controlled. Another 9.25 grams of NaCl was added to the well. The mold was then agitated for an additional 4 minutes. Two grams of salt was then evenly poured over the implant in the well. The mold was left in the air-flow chamber for 24 hours. It was then placed in a heated vacuum at 45° C. and 5000 mTorr for 24 hours. After the 24 hour period, the implants were punched out of the mold with a 10 mm diameter punch. The implants were then placed in distilled water for 72 hours. The water was replaced once daily. The implants were placed in a desiccator at room temperature after they were removed from the water. Constructs were produced having one relatively impermeable side (the top side).

The porosity and permeability of six bone biodegradable fillers were measured following the techniques described above. Permeability was found to be essentially close to zero. Porosity of the impermeable surface was also practically zero.

All United States patents, all foreign patents and all articles cited therein are incorporated herein by reference as if each was incorporated by reference at the time of introduction. Although the invention has been disclosed with reference to its preferred embodiments, from reading this description those of skill in the art may appreciate changes and modification that may be made which do not depart from the scope and spirit of the invention as described above and claimed hereafter.

We claim:

1. A biodegradable tissue filler comprising a continuous polymer matrix including a first region having a first permeability to bodily fluids and a first porosity, a second region having a second permeability to bodily fluids and a second porosity and a third region interposed between the first and second regions having a permeability gradient to bodily fluids and a porosity gradient across a cross-sectional profile of the filler including all three regions, where the matrix comprises at least one biodegradable polymer and the first and second permeabilities are different.

2. The filler of claim 1, wherein the first region is substantially impermeable to bodily fluid to reduce bodily fluid flow from an injured tissue site into adjacent tissue sites, the second region is substantially permeable to bodily fluids and cells to promote tissue repair and regeneration and the third region has increasing permeability to bodily fluids and cells as it transitions from the first region to the second region.

3. The filler of claim 2, wherein the first region is designed to be associated with an outer surface of the injured tissue site and the second region is designed to be associated with an interior of the injured tissue site.

4. The filler of claim 1, wherein the matrix comprises at least two biocompatible polymers having different densities and a composition gradient of the two polymers across the profile.

5. The filler of claim 1, wherein premeability gradient varies smoothly from the first region to the second region.

6. The filler of claim 1, further comprising a coating covering a portion of an outer surface of the filler where the coating is a biodegradable polymer, is substantially impermeable to bodily fluids and is designed to be associated with an outer portion of an injured tissue site to reduce bodily fluid flow into adjacent tissue sites.

7. A method for forming tissue implant composition comprising the steps of:
   a. agitating a mixture comprising at least one polymer and at least one pore-forming agent, where the at least one pore-forming agent and the at least one polymer have different densities;
   b. developing a concentration gradient of the at least one pore-forming agent in the mixture using an applied external force which causes the at least one pore forming agent to migrate through the matrix in response to the applied force; and
   c. leaching the at least one pore-forming agent from the mixture with a leaching reagent to form a tissue implant composition having a concentration gradient of pores, where the leaching reagent is a solvent in which the pore-forming agent is soluble and the at least one polymer is substantially insoluble.

8. The method of claim 7, wherein the mixture further comprising a solvent and the applied force is an applied gravitational force greater than the normal gravitational force or centripetal force.

9. The method of claim 7, wherein the agitating step is performed at a temperature above a softening temperature of the at least one polymer in the mixture.

10. The method of claim 7, further comprising developing a a second concentration gradient of the at least one pore-forming agent in the mixture by the action of a second external force where the first applied force is an enhanced gravitational force and the second force is a centripetal force so that, after the leaching step, a tissue implant composition is formed having a two dimensional concentration gradient of pores.

11. The method of claim 7, further comprising the step of:
   d. subjecting the mixture to a reduced pressure for a time sufficient to remove substantially all of the solvent after step (b).

12. The method of claim 7, further including the steps of:
   d. subjecting the mixture to a first reduced pressure for a first period of time after step (b); and
   e. subjecting the mixture to a second reduced pressure at an elevated temperature for a second period of time; where the sum of the first and second period of time is sufficient to remove substantially all of the solvent.

13. The method of claim 7, wherein the mixture further comprising at least two pore-forming agents having different densities resulting in the formation of two pore gradients corresponding to the at least two pore-forming agents.

14. A method for treating injured tissue sites comprising the steps of inserting into the injured tissue site a biodegradable filler comprising a continuous polymer matrix including a first region having a first permeability to bodily fluids and a first porosity, a second region having a second permeability to bodily fluids and a second porosity and a third region interposed between the first and second regions having a permeability gradient to bodily fluids and a porosity gradient across a cross-sectional profile of the filler including all three regions, where the matrix comprises at least one biodegradable polymer and the first and second permeabilities are different.

15. The method of claim 14, wherein the first permeability is substantially substantially impermeable to bodily fluids and the second permeability is substantially permeable to bodily fluids including cellular constituents thereof.

16. The method of claim 14, wherein the matrix further including a biodegradable coating having substantially no permeable to bodily fluids covering a portion of an outer surface of the filler associated with the outer surface of the injured tissue site.

17. A biodegradable implant comprising a biodegradable polymer matrix having substantial permeability to bodily fluids including cells and cellular constituents and a nonporous biodegradable coating having substantially no permeable to bodily fluids, where the coating covers a portion of an outer surface of the implant and the implant is designed to reduce bodily fluid flow from an injured tissue site into adjacent tissue sites.

18. A method for forming tissue implants comprising the steps of:
   a. agitating a mixture comprising at least one polymer and at least one pore-forming agent comprising particles at a temperature above a softening temperature of the at least one polymer, where the agitation increases a void volume of a pore of surrounding each particle of the pore-forming agent; and
   b. leaching the at least one pore-forming agent from the mixture with a leaching reagent to form a tissue implant having pores, a substantial permeability to bodily fluids and a desired porosity, where the pores have a void volume greater than or equal to the volume of the leached particle.

19. The method of claim 18, further comprising the step of:
   c. coating an outer portion of the implant with a biodegradable polymer that is substantially non-porous and substantially impermeable to bodily fluids so that once implanted bodily fluid flow from an injured tissue site into adjacent tissue sites is reduced.

20. The method of claim 19, wherein the mixture comprises a first pore-forming agents comprising particles having a first size and shape distribution and a second pore-forming agent comprising particles having a second size and shape distribution where the distributions are different.

* * * * *